US00PP34186P2

(12) United States Plant Patent
Bradford et al.

(10) Patent No.: US PP34,186 P2
(45) Date of Patent: May 3, 2022

(54) NECTARINE TREE NAMED 'RED RAGE I'

(50) Latin Name: *Prunus persica*
Varietal Denomination: Red Rage I

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,912

(22) Filed: Dec. 17, 2021

(51) Int. Cl.
*A01H 6/74* (2018.01)
*A01H 5/08* (2018.01)

(52) U.S. Cl.
USPC ..... Plt./190

(58) Field of Classification Search
USPC ..... Plt./190
See application file for complete search history.

(56) References Cited

U.S. PATENT DOCUMENTS

PP15,845 P2 7/2005 Bradford
PP18,715 P2 4/2008 Bradford

*Primary Examiner* — Annette H Para

(57) ABSTRACT

The present invention relates to a new and distinct variety of nectarine tree, *Prunus persica*, broadly characterized by a medium size, vigorous, hardy, self-fertile, productive and regular bearing tree. The variety has a large showy blossom and blooms during the early season, with a chilling requirement of about 500 hours. The fruit matures under the ecological conditions described in late May, with first picking on May 27, 2021. The fruit is uniform, fairly very large in size, acidic and sweet in flavor, very oblate in shape, clingstone in type, firm in texture, yellow in flesh color, full dark red with very minimal freckling in skin color, and has a bitter tasting kernel.

1 Drawing Sheet

Botanical classification: *Prunus persica.*
Variety denomination: 'RED RAGE I'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Red Rage I'.

The present variety was hybridized by us in 2013 as a first generation cross using 'Kay Diamond VII' (U.S. Plant Pat. No. 18,715) nectarine as the selected seed parent and '18P1239' (unpatented) nectarine as the selected pollen parent. Upon reaching maturity the fruit of this hybridization was gathered, and the seeds were removed, cracked, stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2017 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Kay Diamond VII' (U.S. Plant Pat. No. 18,715) nectarine by being vigorous, by being self-fertile, by having a bitter kernel, by requiring about 500 chilling hours, and by producing nectarines that are mostly red in skin color, yellow in flesh color, that are clingstone in type, that are large in size, and that are acidic in flavor, but is quite distinguished from it by having globose leaf glands instead of being eglandular, and by producing nectarines that ripen about five days earlier, that are oblate instead of oblong in shape, and that are somewhat sweeter in flavor.

The present variety is similar to its pollen parent, '8P1239' (unpatented) nectarine, by being self-fertile and by producing nectarines that ripen in late May and that are full red in skin color, oblate in shape, clingstone in type, and firm in texture, but is quite distinguished from it by producing fruit that is larger in size, that is acidic instead of sub-acidic in flavor, and that are yellow instead of white in flesh color.

The present variety is most similar to 'Rose Bright' (U.S. Plant Pat. No. 15,845) nectarine by having a vigorous tree, by having globose leaf glands, by having a large blossom, by being self-fertile, by having a bitter kernel, by having a similar chilling requirement, and by producing nectarines that mature in late May and that are mostly red in skin color, yellow in flesh color, clingstone in type, firm in texture, and acidic in flavor, but is distinguished therefrom by blooming a little earlier and by producing nectarines that are somewhat larger in size, that are more oblate and symmetrical in shape, that have less skin freckling, and that are much sweeter.

SUMMARY OF VARIETY

In summary, the present nectarine variety is characterized by a medium size, vigorous, hardy, self-fertile, productive and regular bearing tree. The variety has a large showy blossom and blooms during the early season, with a chilling requirement of about 500 hours. The fruit matures under the ecological conditions described in late May, with first picking on May 27, 2021. The fruit is uniform, fairly large in size, acidic and sweet in flavor, very oblate in shape, clingstone in type, firm in texture, yellow in flesh color, full dark red with very minimal freckling in skin color, and has a bitter tasting kernel.

DRAWING

The accompanying photograph consists of four whole fruits positioned to display the characteristics of the skin color and form, one divided fruit to reveal the flesh and stone, a tip shoot of new leaf growth, typical leaves, and three insets depicting the flower buds and blossoms as they appear on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 5, 2021, on the original tree during its eighth growing season. The blossom and flower descriptions were made the previous blooming season. All major color code designations are by reference to the Inter-Society Color Council, National Bureau of Standards. Common color names are also used occasionally.

PARENTAGE

Seed parent: 'Kay Diamond VII' (U.S. Plant Pat. No. 18,715) nectarine.

Pollen parent: '8P1239' (unpatented) nectarine.

TREE

Size: Medium, reaching and maintaining a height of 11' [3.35 m.] and a spread of 10' [3.05 m.] after eight growing seasons utilizing typical dormant pruning.

Vigor: Vigorous, responding about average to irrigation and fertilization. The variety grows about 2' [0.61 m.] of surplus top-growth during the spring and summer. The plant should be grown on a standard commercial rootstock for production purposes.

Growth: Spreading and moderately dense.

Form: Pruned to a vase shape.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-fertile.

Bearing: Regular bearer, with no crop failures observed.

Chilling requirement: About 500 hours.

Leaf bud burst: Medium, during the middle of flowering.

Trunk:

- *Size*.—Medium, reaching a maximum diameter of 4¼" [108.0 mm.] after the eighth growing season.
- *Texture*.—Medium to shaggy.
- *Bark color*.—A Light brownish gray [63. l.brGy] and Light grayish brown [60. l.gy.Br] variegation with Grayish brown [61. gy.Br] crevices present.
- *Lenticels*.—Approximate Number Per Square Inch: 8. Color: Brownish orange [54. brO]. Average Size: ⅜" [9.5 mm.] in length. The width is typically one fourth as much as the length. Shape: Elongated.

Branches:

- *Size*.—Slender, diameter of main scaffold is 2½" [63.5 mm.] measured 12" above the crotch, diameter of limb is 1¼" [31.8 mm.] measured 12" above the first fork.
- *Texture*.—Smooth to medium on first and second year wood, increasing in roughness with age.
- *Color*.—1st Year Wood Topside: Grayish red [19. gy.R]. 1st Year Wood Underside: Brilliant yellow green [116. brill.YG]. Older Wood: A Brownish orange [54. brO] and Strong brown [55. s.Br] variegation.
- *Lenticels*.—Number Per Square Inch: About 35 on second year wood. Color: Deep orange [51. deep O]. Average Size: Small, 1/16" [1.6 mm.] in length. The width is typically one fourth as much as the length. Shape: Elongated.

Leaves:

- *Size*.—Medium. Average Length: 5" [127.0 mm.]. Average Width: 1½" [38.1 mm.].
- *Arrangement*.—Alternate.
- *Thickness*.—Medium.
- *Form*.—Elliptical.
- *Apex*.—Acuminate.
- *Base*.—Acute with an average seventy degree angle.
- *Surface*.—Smooth on both sides.
- *Color*.—Dorsal Surface: Moderate olive green [125. m.OlG]. Ventral Surface: Moderate yellow green [120. m.YG].
- *Red midvein*.—Absent.
- *Margin*.—Finely serrate.
- *Venation*.—Pinnately net veined.
- *Petiole*.—Average Length: 7/16" [11.1 mm.]. Average Thickness: 1/16" [1.6 mm.]. Color: Strong yellow green [117. s.YG].
- *Stipules*.—Number: 2 per leaf, up to 6 per growing tip. Average Length: ¼" [6.4 mm.]. Color: Vivid yellow green [115. v.YG] becoming Moderate brown [58. m.Br] with age.
- *Glands*.—Number: 2 to 4 per leaf. Position: Alternate, first pair is located at the intersection of petiole and base of blade. Form: Globose. Size: Medium, about 1/32" [0.8 mm.] in diameter. Color: Strong yellow green [117. s.YG].
- *Leaf buds*.—Pointed.

Flower buds:

- *Hardiness*.—Hardy, with respect to central California blooming season.
- *Diameter*.—Typically ⅜" [9.5 mm.] 1 week before bloom.
- *Length*.—Typically ⅝" [15.9 mm.] 1 week before bloom.
- *Form*.—Not appressed.
- *Surface*.—Pubescent.
- *Tip color*.—Pale purplish pink [252. p.pPk].

Flowers: Perfect, complete, perigynous, usually a single pistil, about thirty stamens, five sepal and petal locations alternately positioned.

- *Type*.—Showy, large.
- *Average flower diameter*.—1⅞" [47.6 mm.].
- *Average flower depth*.—½" [12.7 mm.] when fully open.

*Number of petals*.—Usually five, extra petals and fragments numerous, double blossoms occasional.
*Petal arrangement*.—Overlapping.
*Petal shape*.—Circular to oval.
*Petal margin*.—Entire, slightly wavy.
*Average petal diameter*.—¾" [19.1 mm.].
*Average petal length*.—13/16" [20.6 mm.].
*Petal apex*.—Rounded.
*Petal base*.—Rounded.
*Petal color*.—Light pink [4. l.Pk] toward the apex and Moderate pink [5. m.Pk] toward the base on both sides.
*Anthocyanin coloration intensity*.—Weak.
*Anther color*.—Strong reddish orange [35. s.rO] surrounding a Brilliant yellow [83. brill.Y] center at bloom onset.
*Pollen*.—Anthers produce an abundance of Brilliant yellow [83. brill.Y] pollen.
*Stigma color*.—Light greenish yellow [101. l.gY].
*Stigma position*.—Typically located slightly above the nearby anthers.
*Stamen position*.—Typically located about 1/16" [1.6 mm.] below the petals.
*Average pistil length*.—13/16" [20.6 mm.].
*Average stamen length*.—9/16" [14.3 mm.].
*Ovary*.—Non-pubescent.
*Sepal color*.—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.
*Sepal length*.—⅜" [9.5 mm.].
*Sepal width*.—5/16" [7.9 mm.].
*Sepal apex*.—Rounded to elliptical to match the sepal length and width.
*Sepal margin*.—Fairly smooth.
*Sepal outer surface*.—Pubescent.
*Fragrance*.—Moderate.
*Blooming period*.—Early, blooms about two days before 'May Bright' (U.S. Plant Pat. No. 21,928) nectarine.
*Onset of bloom*.—One percent on Feb. 12, 2021.
*Date of full bloom*.—Feb. 24, 2021.
*Duration of bloom*.—One to two weeks, dependent on ambient temperature.
Bloom density.—Medium to heavy.
*Number per cluster*.—1 to 3 with single flowers most common.

FRUIT

Maturity when described: Firm ripe, Jun. 5, 2021.
Date of first picking: May 27, 2021.
Date of last picking: Jun. 11, 2021.
Size: Uniform, fairly large for early season fruit.
*Average diameter axially*.—2½" [63.5 mm.].
*Average diameter across suture plane*.—3" [76.2 mm.].
*Average diameter across cheek plane*.—2⅞" [73.0 mm.].
*Typical weight*.—7.6 ounces [216 grams].
Form: Uniform, very oblate, mostly symmetrical.
*Longitudinal section form*.—Oblate.
*Axial view*.—Round.
Suture: Extends from the base, along the side, and ends about ½" [12.7 mm.] beyond pistil point.
*Near the base*.—A very shallow groove.
*Along the side*.—A very shallow trough.
*Near the apex*.—A medium groove.
Ventral surface: Rounded, lipped throughout on both sides.
Lips: Mostly unequal.
Cavity: Flaring with Pale yellow [89. p.Y] stem markings present.
*Depth*.—½" [12.7 mm.].
*Breadth*.—1⅛" [28.6 mm.].
Base: Truncate.
Apex: Rounded, cordate if viewed parallel to the suture.
Pistil point: An inconspicuous Yellowish white [92. yWhite] dot depressed within the suture of negligible length.
Stem: Medium.
*Average length*.—⅜" [9.5 mm.].
*Average width*.—3/16" [4.8 mm.].
Skin:
*Thickness*.—Medium.
*Surface*.—Smooth.
*Tenacity*.—Tenacious to the flesh.
*Astringency*.—Astringent.
*Tendency to crack*.—Slight at apex when overripe.
*Color*.—Very deep red [14. v.deep R] over a Deep red [13. deep R] background with minimal Pinkish white [9. pkWhite] freckling toward the apex.
Flesh:
*Color*.—Very orange yellow [66. v.OY] with Moderate red [15. m.R] bleeding and flecking throughout.
*Surface of pit cavity*.—Covered with Very orange yellow [66. v.OY] broken fibers when twisted away from the stone.
*Amygdalin*.—Moderate.
*Juice*.—Abundant.
*Texture*.—Firm.
*Fibers*.—Few, fine, tender.
*Ripens*.—Fairly even, slightly earlier on the shoulders.
*Flavor*.—Tasty blend of acid and sugar, typically 16 brix.
*Aroma*.—Moderate.
*Eating quality*.—Excellent.

STONE

Type: Clingstone.
Form: Oval.
Hilum: Narrow, oblong.
Base: Rounded.
Apex: Acute.
Sides: Mostly Equal.
Tip: Typically 1/16" [1.6 mm.] in length.
Surface: Irregularly furrowed toward the apex, pitted toward the base.
Ridges: Jagged.
External color: Light yellowish brown [76. l.yBr] when first removed.
Pit wall color when cracked: Pale orange yellow [73. p.OY].
Cavity surface color: Light yellowish brown [76. l.yBr].
Average pit wall thickness: ¼" [6.4 mm.].
Average length: 1 5/16" [33.3 mm.].
Average width: 1⅛" [28.6 mm.].
Average breadth: ⅞" [22.2 mm.].
Tendency to split: None observed.
Kernel:
*Form*.—Oval.
*Skin color*.—Dark yellow [88. d.Y].
*Pellicle color*.—Moderate olive brown [95. m.OlBr].
*Vein color*.—Light yellow [86. l.Y].
*Taste*.—Bitter.
*Viable*.—Yes.

*Average length.*—¾" [19.1 mm.].
*Average width.*—9/16" [14.3 mm.].
*Amygdalin.*—Abundant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described.

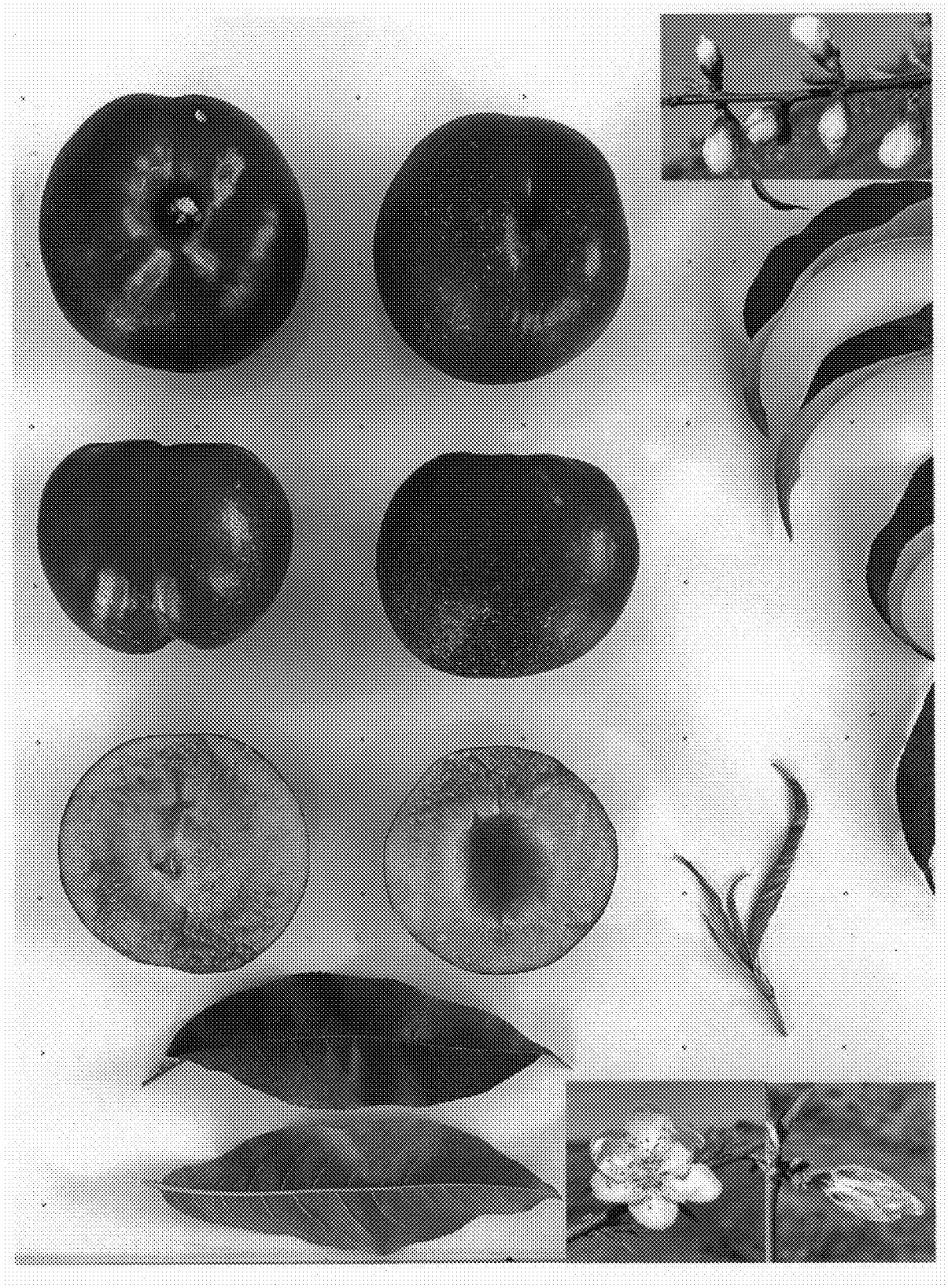

* * * * *